(12) United States Patent
Hastings et al.

(10) Patent No.: US 8,734,508 B2
(45) Date of Patent: May 27, 2014

(54) SYSTEMS AND METHODS FOR MAKING AND USING PERCUTANEOUSLY-DELIVERED PUMPING SYSTEMS FOR PROVIDING HEMODYNAMIC SUPPORT

(75) Inventors: Roger N. Hastings, Maple Grove, MN (US); Michael J. Pikus, Golden Valley, MN (US); Scott Raymond Smith, Chaska, MN (US); Leonard B. Richardson, Brooklyn Park, MN (US); Kevin D. Edmunds, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 499 days.

(21) Appl. No.: 12/967,856

(22) Filed: Dec. 14, 2010

(65) Prior Publication Data

US 2011/0152999 A1 Jun. 23, 2011

Related U.S. Application Data

(60) Provisional application No. 61/288,719, filed on Dec. 21, 2009.

(51) Int. Cl.
*A61M 1/10* (2006.01)

(52) U.S. Cl.
USPC .......................................................... 623/3.1

(58) Field of Classification Search
USPC .......................................................... 623/3.1
See application file for complete search history.

(56) References Cited

U.S. PATENT DOCUMENTS 7,396,327 B2 * 7/2008 Morello .......................... 600/17

* cited by examiner

*Primary Examiner* — Thomas J Sweet
*Assistant Examiner* — Matthew Schall
(74) *Attorney, Agent, or Firm* — Seager, Tufte & Wickhem, LLC

(57) ABSTRACT

A percutaneous pumping system for providing hemodynamic support to a patient includes a pumping sleeve that defines a lumen extending along the length of the pumping sleeve. The pumping sleeve is configured and arranged for insertion into patient vasculature. At least one rotatable magnet is disposed in the pumping sleeve. The at least one first magnet is configured and arranged to be driven to rotate by a magnetic field generated external to the pumping sleeve. At least one impeller is coupled to the at least one magnet. Rotation of the at least one magnet causes a corresponding rotation of the at least one impeller. An anchoring arrangement is coupled to the pumping sleeve. The anchoring arrangement is configured and arranged to anchor the pumping sleeve at a target pumping location when the pumping sleeve is inserted into patient vasculature.

18 Claims, 8 Drawing Sheets

US 8,734,508 B2

SYSTEMS AND METHODS FOR MAKING AND USING PERCUTANEOUSLY-DELIVERED PUMPING SYSTEMS FOR PROVIDING HEMODYNAMIC SUPPORT

CROSS-REFERENCE TO RELATED APPLICATIONS

This application claims the benefit under 35 U.S.C. §119 (e) of U.S. Provisional Patent Application Ser. No. 61/288,719 filed on Dec. 21, 2009, which is incorporated herein by reference.

TECHNICAL FIELD

The present invention is directed to the area of hemodynamic support systems and methods of making and using the systems. The present invention is also directed to hemodynamic support systems having percutaneously-delivered pumping systems powered by magnetic motors, as well as methods for making and using the hemodynamic support systems, percutaneously-delivered pumping systems, and magnetic motors.

BACKGROUND

Hemodynamic support may be used to provide perfusion of patient tissues in order to supply the tissues with oxygen and nutrients and remove undesired wastes. For example, hemodynamic support is provided for patients with either temporary or long-term inadequate blood circulation. Hemodynamic support has been provided to patients in cardiogenic shock (e.g., from primary failure of the ventricles of the heart), patients recovering from cardiac surgery (e.g., post acute myocardial infarction), and patients with acute decompensated heart failure.

BRIEF SUMMARY

In one embodiment, a percutaneous pumping system for providing hemodynamic support to a patient includes a pumping sleeve having a length, a distal end, and a proximal end. The pumping sleeve defines a lumen extending along the length of the pumping sleeve from the proximal end to the distal end. The pumping sleeve is configured and arranged for insertion into patient vasculature. At least one rotatable magnet is disposed in the pumping sleeve. The at least one first magnet is configured and arranged to be driven to rotate by a magnetic field generated external to the pumping sleeve. At least one impeller is coupled to the at least one magnet. Rotation of the at least one magnet causes a corresponding rotation of the at least one impeller. An anchoring arrangement is coupled to the pumping sleeve. The anchoring arrangement is configured and arranged to anchor the pumping sleeve at a target pumping location when the pumping sleeve is inserted into patient vasculature.

In another embodiment, a percutaneous pumping system for providing hemodynamic support to a patient includes an expandable stent configured and arranged for insertion into patient vasculature. At least one rotatable magnet is disposed in the expandable stent. The at least one first magnet is configured and arranged to be driven to rotate by a magnetic field generated external to the expandable stent. The at least one magnet rotates about a shaft. At least one impeller is coupled to the at least one magnet such that rotation of the at least one magnet causes a corresponding rotation of the at least one impeller. At least one strut couples the at least one shaft to the expandable stent to anchor the at least one magnet within the expandable stent.

In yet another embodiment, a method for providing hemodynamic support for a patient includes inserting a percutaneous pumping system into patient vasculature. The percutaneous pumping system includes a pumpingسleeve having a length, a distal end, and a proximal end. The pumping sleeve defines a lumen extending along the length of the pumping sleeve from the proximal end to the distal end. At least one rotatable magnet is disposed in the pumping sleeve. The at least one magnet is configured and arranged to be driven to rotate by a magnetic field generated external to the pumping sleeve. At least one impeller is coupled to the at least one magnet such that rotation of the at least one magnet causes a corresponding rotation of the at least one impeller. The percutaneous pumping system is anchored to a target pumping location within the patient vasculature using an anchoring arrangement coupled to the pumping sleeve. A magnetic field is generated to cause the at least one magnet to rotate.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
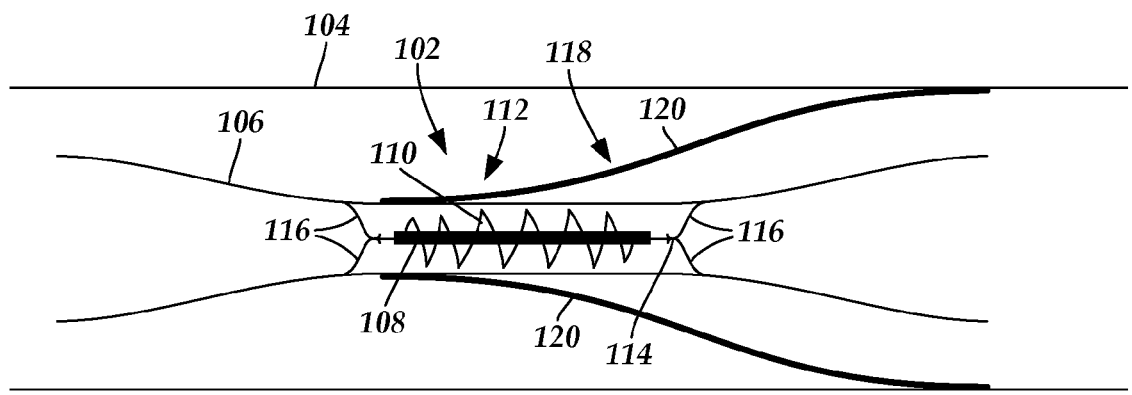
FIG. 1 is a schematic longitudinal cross-sectional view of one embodiment of a pumping assembly positioned in patient vasculature, according to the invention.

The present invention is directed to the area of hemodynamic support systems and methods of making and using the systems. The present invention is also directed to hemodynamic support systems having percutaneously-delivered pumping systems powered by magnetic motors, as well as methods for making and using the hemodynamic support systems, percutaneously-delivered pumping systems, and magnetic motors.

A percutaneous pumping system ("blood pump") for providing at least partial hemodynamic support to a patient utilizes a magnetic motor to supply power to pump fluid (e.g., blood) within patient vasculature. In at least some embodiments, the blood pump pumps at least 5 liters of blood per minute without causing excessive heat build-up (i.e., without producing enough sustained heat to cause tissue damage). In at least some embodiments, the blood pump includes a pumping assembly and an external stator. In at least some embodiments, the pumping assembly is configured and arranged for insertion into a patient via an insertion device with a bore that is no greater than 9 French. In at least some embodiments, the pumping assembly is configured and arranged to reduce non-uniform rotation distortion caused by patient tissue pressing against the blood pump, such as at a bend in patient vasculature.

The blood pump includes a magnetic motor that includes a rotor and a stator. The rotor is a rotatable magnet. In at least some embodiments, the stator includes a plurality of magnetic field windings configured and arranged to rotate the magnet by generating a rotating magnetic field. In at least some embodiments, the windings are positioned external to a pumping assembly containing the magnet and a pumping sleeve or stent. In at least some embodiments, the windings are positioned external to patient vasculature. In at least some embodiments, the windings are positioned external to the cardiovascular system of the patient. In at least some embodiments, the windings are subcutaneously implanted in the patient. In at least some embodiments, the windings are positioned external to the patient.

It may be an advantage to position the windings external to the patient. Externally positioned windings are not wrapped over an outer surface of the magnet. Thus, the diameter of a pumping assembly (and an associated insertion device), which is insertable into the patient, may be smaller. Blood pumps using extracorporeal windings may be insertable into patient vasculature that was previously too small to be accessed with conventional blood pump systems.

Extracorporeal windings may also have the advantage of eliminating the inclusion of motor conductors within the patient for providing power to operate the motor. Moreover, another potential advantage to extracorporeal windings is that the windings may be formed from lower-cost materials than internal windings because the windings may not be miniaturized or do not need to be fabricated from materials suitable for insertion into a patient. In at least some embodiments, suitable extracorporeal windings do not need to be cooled or use superconductors to generate a large enough magnetic field to drive rotation of the magnet. Additionally, when an imaging system uses windings that are cooled or use superconductors (e.g., to generate a larger magnetic field, or the like), it is typically easier to cool the windings or use superconductors when the windings are disposed external to a patient than when the windings are disposed within a patient.

In at least some embodiments, the pumping assembly may be inserted percutaneously into a patient via an accessible blood vessel, such as the femoral artery, at a site remote from the target pumping location. The pumping assembly may be guided to many different target pumping locations, such as the left ventricle, the aortic valve, the ascending aorta, the descending aorta, or the like.

In at least some embodiments, the pumping assembly is delivered to a target pumping location by an insertion device (e.g., an introducer sheath, a guidewire, or the like). In at least some embodiments, the pumping assembly is configured and arranged for percutaneous insertion into a patient by an insertion device having a bore that is no greater than 11 French. In at least some embodiments, the pumping assembly is configured and arranged for percutaneous insertion into a patient by an insertion device having a bore that is no greater than 10 French. In at least some embodiments, the pumping assembly is configured and arranged for percutaneous insertion into a patient by an insertion device having a bore that is no greater than 9 French. In at least some embodiments, the pumping assembly is configured and arranged for percutaneous insertion into a patient by an insertion device having a bore that is no greater than 8 French.

In at least some embodiments, the pumping assembly includes a pumping sleeve, a rotation apparatus disposed in the pumping sleeve, and an anchoring arrangement for maintaining the position of the pumping sleeve at a target pumping location during operation. In at least some embodiments, the rotation system is configured and arranged such that rotation of the magnet causes a corresponding rotation of one or more impellers. In at least some embodiments, the one or more impellers are configured and arranged to expand upon release from an insertion device. The one or more impellers may be formed from any materials suitable for implantation and expansion from an insertion device including, for example, shape memory metal or metal mesh material covered with one or more polymers. In at least some embodiments, the shape memory metal is magnetic. In at least some embodiments, the shape memory metal is formed as a permeable magnet. In at least some embodiments, the shape memory metal is formed as a permanent magnet.

In at least some embodiments, the one or more impellers have expanded diameters of at least 10 mm. In at least some embodiments, the one or more impellers have expanded diameters of at least 11 mm. In at least some embodiments, the one or more impellers have expanded diameters of at least 12 mm. In at least some embodiments, the one or more impellers have expanded diameters of at least 13 mm. In at least some embodiments, the one or more impellers have expanded diameters of at least 14 mm.

In at least some embodiments, the pumping assembly is configured and arranged for temporary insertion into the patient. In at least some embodiments, the pumping assembly is configured and arranged to be removed when hemodynamic support is no longer needed by the patient. In at least some embodiments, the pumping assembly may be retrieved once hemodynamic support is no longer needed by the patient. In at least some embodiments, a retrieval device, such as a retrieval sheath, may be used to retrieve the pumping assembly. In at least some embodiments, the retrieval device expands to a diameter that is larger than a diameter of the pumping sleeve. In at least some embodiments, magnetic attraction may be used between the pumping assembly and the retrieval device. For example, a magnet may be disposed on one of the pumping assembly or the retrieval device and a magnetic material may be disposed on the other of the pumping assembly or the retrieval device. In at least some embodiments, a safety line may be used to facilitate removal of the pumping assembly. In at least some embodiments, one end of the safety line is attached to the pumping assembly and the other end of the safety line extends from the entry point of the pumping assembly into the patient.

FIG. 1 is a schematic longitudinal cross-sectional view of one embodiment of a pumping assembly 102 positioned in patient vasculature, such as a patient's descending aorta 104. The pumping assembly 102 includes an elongated pumping sleeve 106. One or more rotatable magnets 108 and one or more impellers 110 are disposed in the pumping sleeve 106. The one or more impellers 110 are coupled to the one or more magnets 108 such that rotation of the one or more magnets 108 causes a corresponding rotation of the impellers 110. In at least some embodiments, the one or more impellers 110 are directly coupled to the one or more magnets 108. In at least some embodiments, the one or more impellers 110 are disposed, at least partially, over the one or more magnets 108.

In at least some embodiments, the one or more magnets 108 are coupled to a magnet support structure 112 that includes a shaft 114 on which the one or more magnets 108 rotate and one or more struts 116 securing the one or more magnets 108 to the pumping sleeve 106. In at least some embodiments, the shaft 114 does not extend beyond the pumping sleeve 106. In at least some embodiments, the shaft 114 is coupled directly to the one or more struts.

In at least some embodiments, the shaft 114 is a driveshaft that rotates with the one or more impellers 110. In at least some embodiments, such as when the shaft 114 is a driveshaft, the shaft 114 is coupled to the one or more struts 116 via bushings or jewel bearings (not shown). In at least some embodiments, the one or more struts 116 are configured and arranged to expand upon release from an insertion device. In at least some embodiments, the one or more struts 116 expand such that the one or more magnets 108 are transversely centered within the pumping sleeve 106.

In alternate embodiments, the shaft 114 extends from at least one of the ends of the one or more magnets 108. In at least some embodiments, at least one of the one or more impellers 110 is disposed on one of the portions of the shaft 114 extending from one of the ends of the one or more magnets 108. In at least some embodiments, at least one of the one or more impellers 110 is positioned axially from the one or more magnets 108 within the pumping sleeve 106.

The pumping assembly 102 also includes an anchoring arrangement 118 for maintaining the positioning of the pumping sleeve 106 at the target pumping location during operation. In at least some embodiments, the anchoring arrangement 118 includes one or more expandable struts 120 that expand to anchor the pumping assembly 102 to patient vasculature, such as an inner wall of the descending aorta 104.

In at least some embodiments, the target pumping location is the descending aorta. In at least some embodiments, the pumping assembly 102 is delivered to a target pumping location in the descending aorta that is superior to the renal arteries. In at least some embodiments, the pumping assembly 102 is delivered to a target pumping location in the descending aorta that is proximal to the renal arteries. In at least some embodiments, the target pumping location is in the ascending aorta. In at least some embodiments, the target pumping location is in both the ascending aorta and the descending aorta. In at least some embodiments, the target pumping location is in the vena cava. In at least some embodiments, the target pumping location is in a proximal coronary, carotid, or renal artery. In at least some embodiments, the target pumping location is in a proximal femoral or saphenous vein. In at least some embodiments, the target pumping location is in another blood vessel within patient vasculature. In at least some embodiments, the target pumping location is in another location in the cardiovascular system.

In at least some embodiments, the anchoring arrangement 118 is configured and arranged to expand upon release from an insertion device. In at least some embodiments, the anchoring arrangement 118 is configured and arranged to anchor the pumping assembly to the target pumping location such that the pumping sleeve 106 is transversely centered within a lumen of the target pumping location, such as the descending aorta 104.

In at least some embodiments, the pumping assembly 102 is configured and arranged to pump blood downstream to facilitate perfusion of the lower peripheral arteries. In at least some embodiments, the pumping assembly 102 is configured and arranged to pump blood upstream to one or more arterial branches of the aortic arch to facilitate perfusion of the coronary, cerebral, and upper peripheral arteries. In at least some embodiments, the pumping assembly 102 is configured and arranged to alternately pump blood upstream and downstream. In at least some embodiments, the pumping assembly 102 is configured and arranged to pump blood downstream during systole and upstream during diastole.

Figure 2:
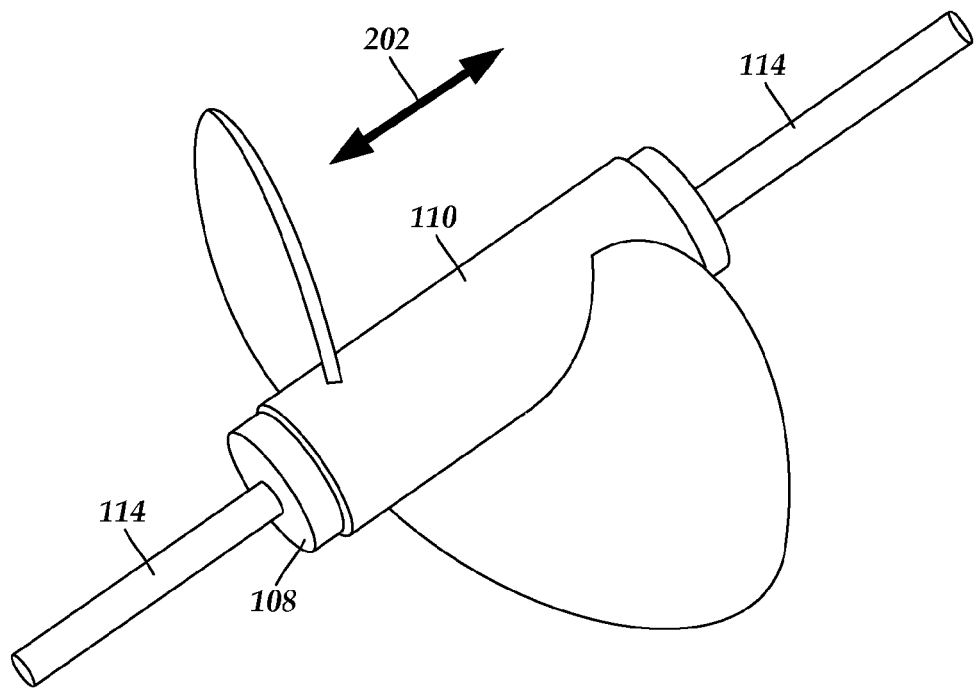
FIG. 2 is a schematic close-up perspective view of one embodiment of an impeller disposed over a magnet rotating on a shaft, according to the invention.

FIG. 2 is a schematic close-up perspective view of one embodiment of a magnet 108 rotating on the shaft 114. In FIG. 2, the impeller 110 is shown disposed over the magnet 108. In at least some embodiments, the one or more magnets 108 define a longitudinal axis 202, shown in FIG. 2 as a two-headed arrow. In at least some embodiments, the longitudinal axis 202 of the one or more magnets 108 is parallel to a longitudinal axis of the pumping sleeve 106. In at least some embodiments, the longitudinal axis 202 of the one or more magnets 108 is parallel with the directionality of blood flow of the target pumping location within which the one or more magnets 108 is disposed.

In at least some embodiments, the one or more magnets 108 are cylindrical. In at least some embodiments, the one or more magnets 108 each have a magnetization M of no less than 1.4 T. In at least some embodiments, the one or more magnets 108 each have a magnetization M of no less than 1.5 T. In at least some embodiments, the one or more magnets 108 each have a magnetization M of no less than 1.6 T. In at least some embodiments, the one or more magnets 108 each have a magnetization vector that is perpendicular to the longitudinal axis of the one or more magnets 108.

In at least some embodiments, the one or more magnets 108 each have a diameter that is no greater than 3 mm. In at least some embodiments, the one or more magnets 108 each have a diameter that is no greater than 2.5 mm. In at least some embodiments, the one or more magnets 108 each have a diameter that is no greater than 2 mm. In at least some embodiments, the one or more magnets 108 each have a diameter that is no greater than 1.5 mm. In at least some embodiments, the one or more magnets 108 each have a diameter that is no greater than 1 mm. In at least some embodiments, the one or more magnets 108 each have a length that is at least 12 mm. In at least some embodiments, the one or more magnets 108 each have a length that is at least 13 mm. In at least some embodiments, the one or more magnets 108 each have a length that is at least 14 mm. In at least some embodiments, the one or more magnets 108 each have a length that is at least 15 mm. In at least some embodiments, the one or more magnets 108 each have a length that is at least 16 mm. In at least some embodiments, the one or more magnets 108 each have a length that is at least 17 mm. It will be understood that larger or smaller magnets may also be used.

A magnetic field generated by externally positioned windings causes the one or more magnets 108 to rotate about the longitudinal axis 202 of the one or more magnets 108. An applied current creates the rotating magnetic field in the windings. In at least some embodiments, the one or more magnets 108 are permanent magnets. The one or more magnets 108 may be formed from many different magnetic materials suitable for implantation including, for example, neodymium-iron-boron, or the like. One example of a suitable neodymium-iron-boron magnet is available through Hitachi Metals America Ltd, San Jose, Calif.

The windings provide a rotating magnetic field to produce a torque on the one or more magnets 108. Two or more windings oriented parallel to the longitudinal magnet axis 108 wrap around the ends one or more magnets 108 as one or more turns to form a rotating magnetic field. The windings may be powered from any suitable power source (e.g., an external control module, batteries, or other power source).

Figure 3:
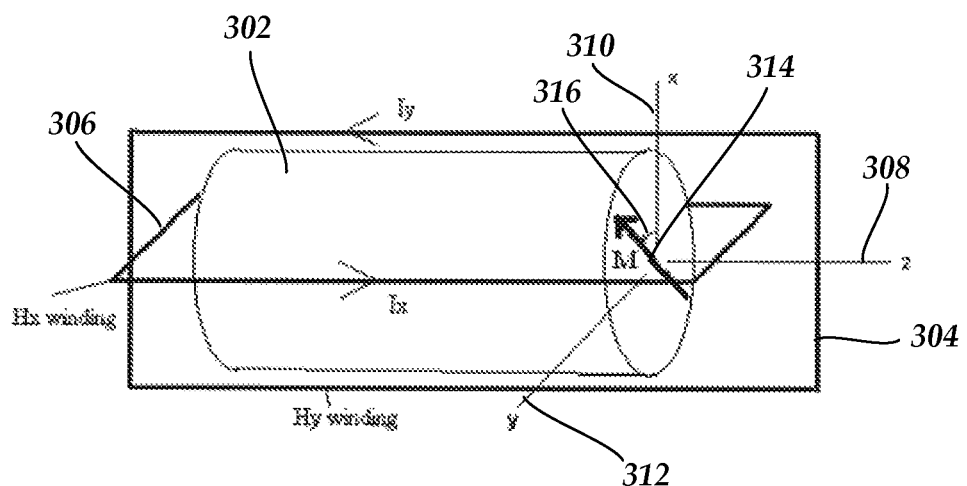
FIG. 3 is a schematic perspective view of one embodiment of a rotating magnet and associated magnetic field windings, according to the invention.

FIG. 3 is a schematic perspective view of one embodiment of an exemplary rotatable magnet 302 and associated windings, represented as orthogonal rectangular boxes 304 and 306. Although the windings 304 and 306 are shown as two orthogonal rectangles, it will be understood that the each of the windings 304 and 306 may represent multiple turns of wire. When the windings 304 and 306 are spread out, a band of current may be generated instead of the lines of current shown in FIG. 3. It will also be understood that, as discussed below, there may be more than two orthogonal windings. For example, as discussed above and below, (e.g., 108 in FIG. 1; 1108 in FIG. 11; 1210 and 1214 in FIG. 12; and 1308 in FIG. 13) may be rotated by one or more windings.

The magnet 302 has a longitudinal (z) axis 308 about which the magnet 302 rotates. In order for the magnet 302 to rotate about the longitudinal axis 308, the torque must be about the longitudinal axis 308. Therefore, the magnetic field generated by the windings 304 and 306 must lie in a plane perpendicular to the longitudinal axis 308 with a magnetic field vector H for the windings 304 and 306 rotating about the longitudinal (z) axis 308 to torque and rotate the magnet 302. FIG. 3 also shows an x-axis 310 and a y-axis 312 that are orthogonal to each other and to the longitudinal axis 308. As shown in FIG. 3, the magnetization vector M 314 of the magnet 302 is in an x-y plane that is perpendicular to the longitudinal axis 308. The winding 304 produces a magnetic field at the center of the winding 304 that is parallel to the y-axis 312. The winding 306 produces a magnetic field at the center of the winding 306 that is parallel to the x-axis 310.

Figure 4:
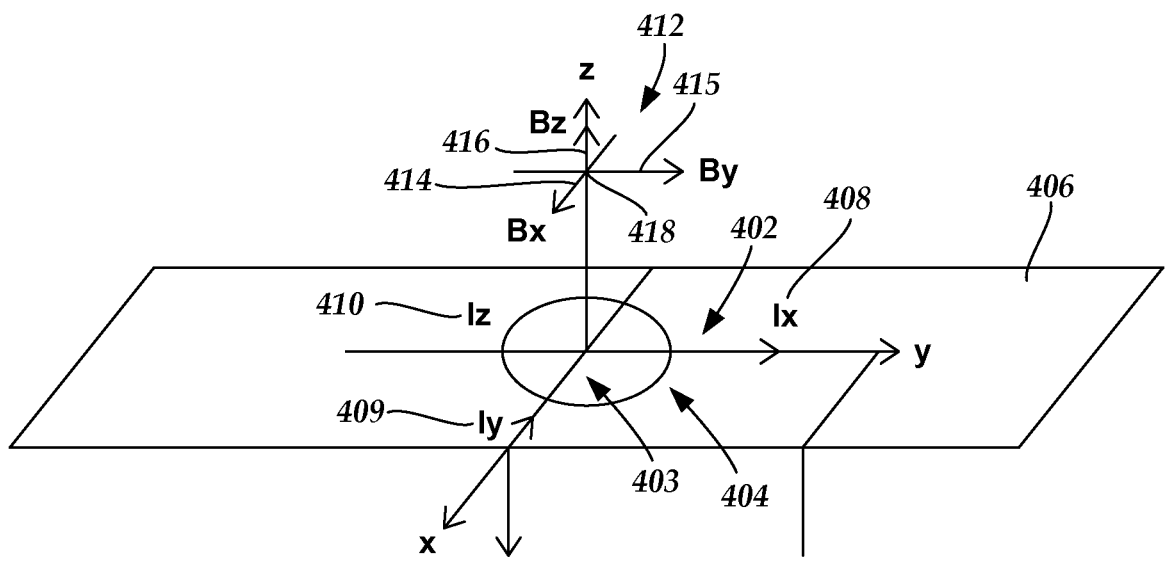
FIG. 4 is a schematic perspective view of one embodiment of portions of three orthogonal magnetic field windings positioned on a plane that form a magnetic field above the plane, according to the invention.

As discussed above, in at least some embodiments the windings are disposed external to the patient into which the magnet is disposed. The extracorporeal windings form a magnetic field within the patient at a target pumping site. FIG. 4 is a schematic perspective view of one embodiment of portions of three orthogonal windings 402-404 positioned on a plane 406. Currents Ix 408, Iy 409, and Iz 410 transmit through the portions of the orthogonal windings 402-404, respectively, as shown by arrows. When currents 408-410 are transmitted through the windings 402-404 in the directions indicated, a magnetic field 412 is formed having three orthogonal components Bx 414, By 415, and Bz 416, respectively, at the intersection 418 of the orthogonal components Bx 414, By 415, and Bz 416. In at least some embodiments, the intersection 418 represents a hypothetical location of a rotatable magnet (see e.g., 108 in FIG. 1) within a patient. In at least some embodiments, the portions of the windings 402 and 403 positioned on the plane 406 are straight. In at least some embodiments, the portion of the winding 404 positioned on the plane 406 is a circular loop.

In at least some embodiments, the plane 406 is positioned within a surface suitable for supporting a patient. In at least some embodiments, the plane 406 is positioned above or below a surface suitable for supporting a patient. In at least some embodiments, the windings 402-404 are configured such that the magnetic field 412 is formed within the patient lying on the surface. In at least some embodiments, the magnetic field 412 has a constant amplitude.

Each of the portions of the orthogonal windings 402-404 positioned on the plane 406 includes a return path (not shown). The return paths of the windings 402-404 may be in any configuration. In preferred embodiments, the return paths are positioned away from the portions of the windings 402-404 positioned on the plane 406. It will be understood that each of the windings 402-404 represents one or more turns of a wire.

When the magnetic field 412 is formed at a height (z) above the plane 406, the magnetic field 412 is given by:

$$H_{x,y} = NI_{x,y}/(2\pi z);$$

and $$H_z = NI_z/(D[1+(2z/D)^2]^{3/2});$$

It will be appreciated that adjusting the currents $I_x$, $I_y$ and $I_z$ independently allows the above magnetic field components to take on any value. In particular, the magnetic field vector may be directed perpendicular to the axis of a pump magnet located at point z. By varying the field components over time, the magnetic field may be rotated about the longitudinal axis of a pump magnet located at point z.

In at least some embodiments, z is formed at a location such that the magnetic field is within a patient lying on a surface at, or adjacent to, the plane 406. For example, when a target pumping location is the patient's aorta, and when the patient is lying on a surface at, or adjacent to, the plane 406, z, in this example, is no greater than approximately 0.3 meters. In one embodiment, N=200 and $I_{x,y}$=3 amps, where N=the number of turns in the winding. In at least some embodiments, the windings 402-404 are formed from stranded wire that forms a flexible band of current.

Figure 5:
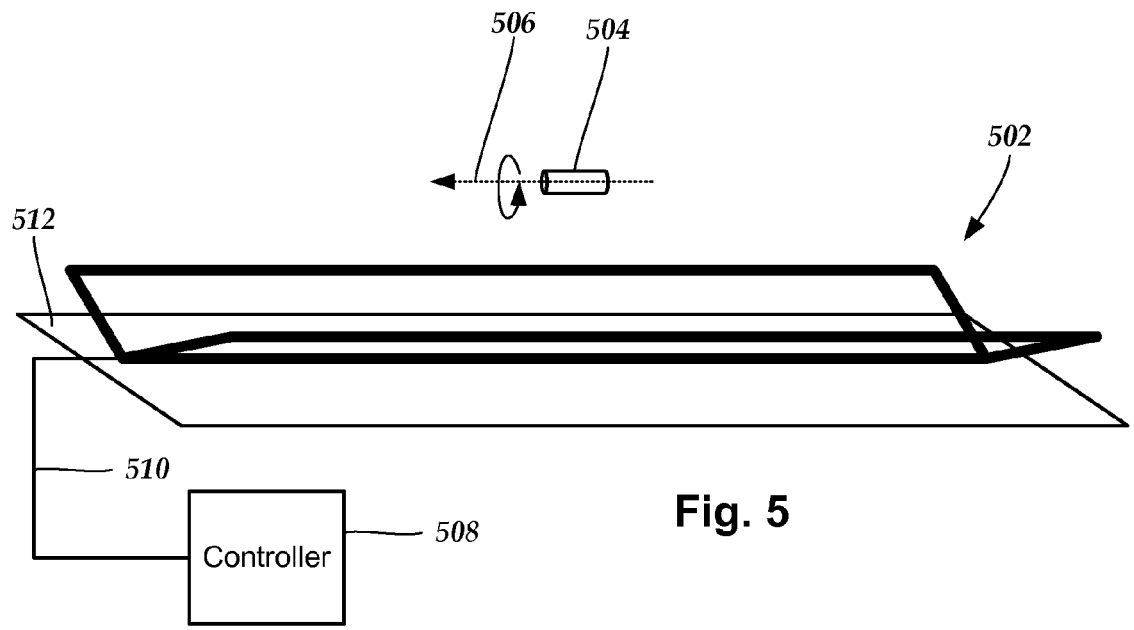
FIG. 5 is a schematic perspective view of one embodiment of a stator winding disposed above a bed driving a motor magnet, according to the invention.

FIG. 5 is a schematic perspective view of one embodiment of a three-phase winding 502 generating a magnetic field that drives rotation of a motor magnet 504 around a longitudinal axis 506 of the magnet 504. A controller 508 is coupled to the three-phase winding 502 by one or more conductors 510. In at least some embodiments, the controller 508 provides power for generating the magnetic field. In FIG. 5, the three-phase winding 502 is shown disposed on a plane 512. In at least some embodiments, the plane 512 is a bed on which a patient may lie. In at least some embodiments, the three-phase winding 502 may be repositioned to allow patient access to the bed. In at least some embodiments, the three-phase winding 502 may be used by the patient as a bed railing, an arm rest, or the like during a procedure.

Figure 6:
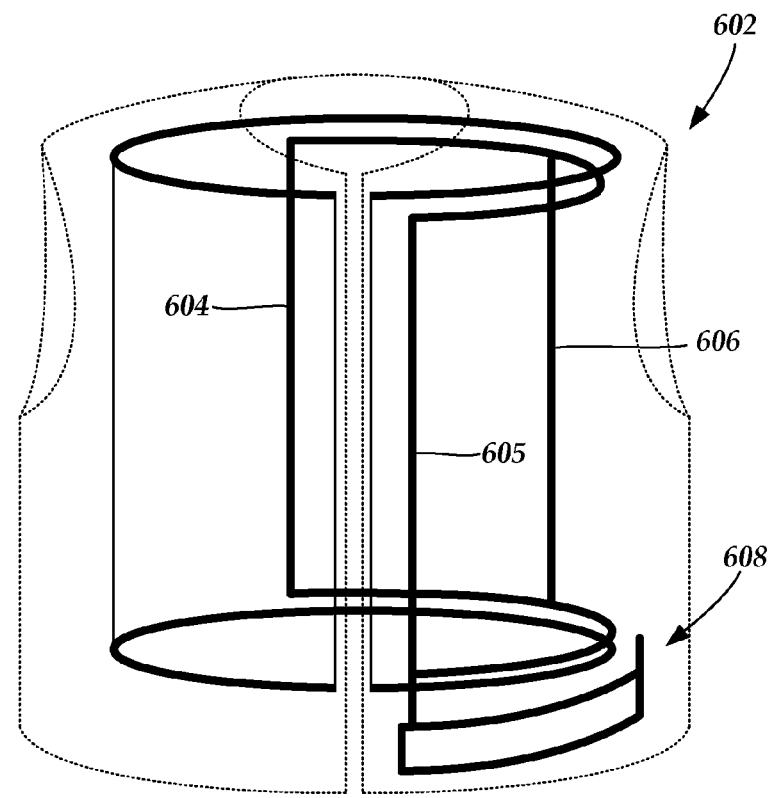
FIG. 6 is a schematic perspective view of one embodiment of a stator winding disposed in a vest, according to the invention.

In alternate embodiments, the windings are disposed in a garment that may be worn by a patient. FIG. 6 is a schematic view of one embodiment of a vest 602 (shown in dotted lines) that may be worn by a patient. The vest 602 includes three-phase winding 604-606. In at least some embodiments, the vest 602 includes a controller 608 coupled to the vest 602. In at least some embodiments, the controller 608 includes an electronic subsystem for controlling one or more operations of the blood pump, such as drive electronics and controls. In at least some embodiments, the controller 608 includes a power supply, such as one or more batteries. It will be understood that the three-phase winding 604-606 may be incorporated into many different types of garments besides vests including, for example, jackets, coats, sweaters, shirts, overalls, coveralls, robes, wraps, or the like.

In at least some embodiments, the windings are formed from rigid or semi-rigid materials using multiple-phase winding geometries. It will be understood that there are many different multiple-phase winding geometries and current configurations that may be employed to form a rotating magnetic field. For example, the windings may include, for example, a two-phase winding, a three-phase winding, a four-phase winding, a five-phase winding, or more multiple-phase winding geometries. It will be understood that a motor may include many other multiple-phase winding geometries. In a two-phase winding geometry, for example, the currents in the two windings are out of phase by 90°. For a three-phase winding, there are three lines of sinusoidal current that are out of phase by zero, 120°, and 240°, with the three current lines also spaced by 120°, resulting in a uniformly rotating magnetic field that can drive a cylindrical rotor magnet magnetized perpendicular to the current lines.

Figure 7:
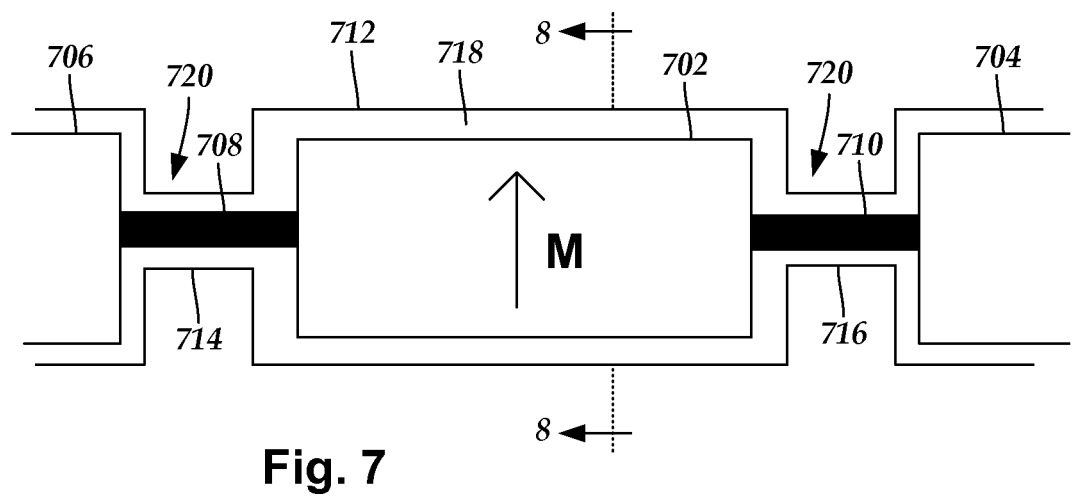
FIG. 7 is a schematic longitudinal cross-sectional view of one embodiment of a link magnet electrically coupled in series to other link magnets via electrical interconnects, according to the invention.

In at least some embodiments, the magnet may include a plurality of link magnets coupled to one another in series. FIG. 7 is a schematic longitudinal cross-sectional view of one embodiment of a link magnet 702 mechanically coupled in series to other link magnets 704 and 706 via a flexible drive shaft 720 that includes flexible drive shaft segments 708 and 710, respectively. Magnets 702, 704, and 706 are surrounded by a flexible sheath 712. The wall of sheath 712 contains three lines of electrical conductors that form a three phase winding. In at least some embodiments, one or more movement limiting structures may be disposed at one or more locations anywhere along the sheath. In FIG. 7, indents 714 and 716 are positioned between the link magnets. The indents 714 and 716 serve as stops that limit longitudinal movements of the magnets relative to the sheath. The indents 714 and 716 contain the three phase windings, continuing the flow of current down the length of the sheath.

Figure 8:
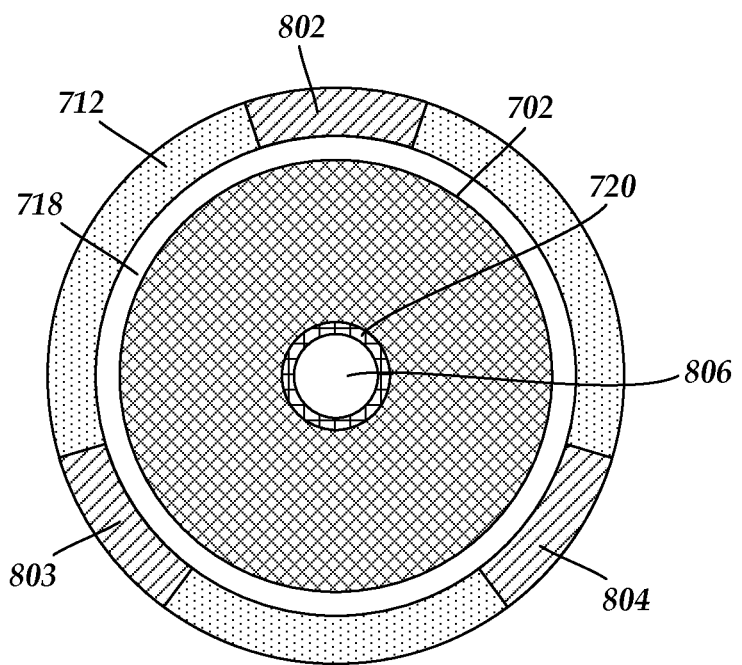
FIG. 8 is a schematic transverse cross-sectional view of one embodiment of one of the link magnets of FIG. 7, according to the invention.

FIG. 8 is a schematic transverse cross-sectional view of one embodiment of the link magnet 702. In at least some embodiments, a sheath 712 is disposed over the link magnets 702, 704, and 706. Electrical windings 802, 803, and 804 carry three phase currents that apply equal torques to magnets 702, 704, and 706. In at least some embodiments, the link magnet 702 is mechanically coupled to link magnets 704 and 706 via the flexible drive shaft 720. In at least some embodiments, the flexible drive shaft 720 rotates along with magnets 702, 704, and 706 over a guidewire (not shown) which passes through the center lumen 806 of the flexible drive shaft 720.

In at least some embodiments, a gap 718 may be formed between the link magnet 702 and the sheath 712. In at least some embodiments, the gap 718 may be at least partially filled with lubricant to reduce friction as the link magnet 702 rotates against a non-rotating sheath 712. In at least some embodiments, the lubricant is a magnetic fluid (e.g., a ferrofluid, or the like) that adheres to the link magnet 702 and shears at or near the sheath 712 when the link magnet 702 rotates.

Motor torque is proportional to the product of the number of link magnets and the length of each link magnet. Motor torque is also proportional to the diameters of the link magnets. Thus, a sliding scale relationship exists between the number of magnet links and the size of the link magnets. For example, when the size of the link magnets is reduced, the number of link magnets may increase to produce a given amount of motor torque on the flexible drive shaft 720.

Figure 9:
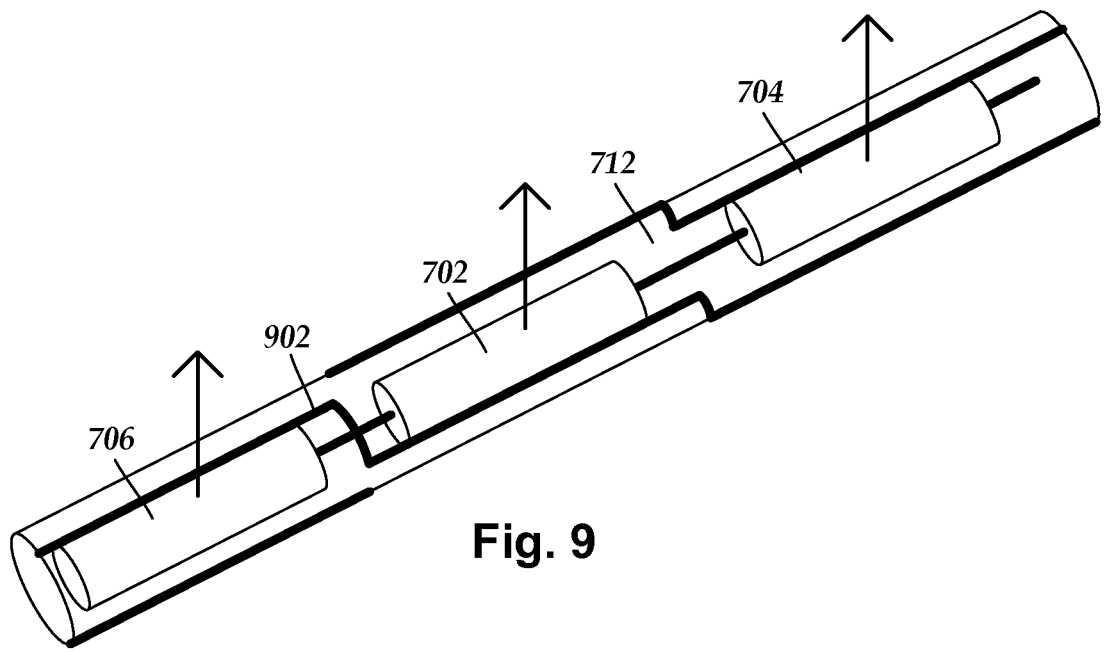
FIG. 9 is a schematic perspective view of one embodiment of stator windings arranged in a staggered configuration and disposed along a sheath disposed over the link magnets of FIG. 7, according to the invention.

As discussed above, rotation of the link magnets 702, 704, and 706 may be powered by a magnetic field generated by external stator windings as described for the previous embodiments. It will be understood, however, that in alternate embodiments rotation of the link magnets 702, 704, and 706 may be powered by stator windings disposed in the sheath 712. For example, FIG. 9 is a schematic perspective view of one embodiment of windings 902 disposed along the sheath 712 in a staggered configuration. When motor torque is applied to the flexible drive shaft 720, the motor torque may be designed to twist the flexible drive shaft 720 along its length. The staggered configuration of windings 902 are configured and arranged to compensate for drive shaft twisting so that the angle between the magnetic field of the windings and the individual magnet magnetization vectors is the same for each magnet. Thus the torque exerted by each magnet on the drive shaft is the same for each magnet as the drive shaft rotates. In alternate embodiments, the windings 902 may extend linearly along a longitudinal axis of the sheath 712. Twisting of the flexible drive shaft 720 may also be compensated for by forming a distal end of the sheath 712 such that the distal end of the sheath 712 is twisted to form a spiral configuration of the windings.

Figure 10:
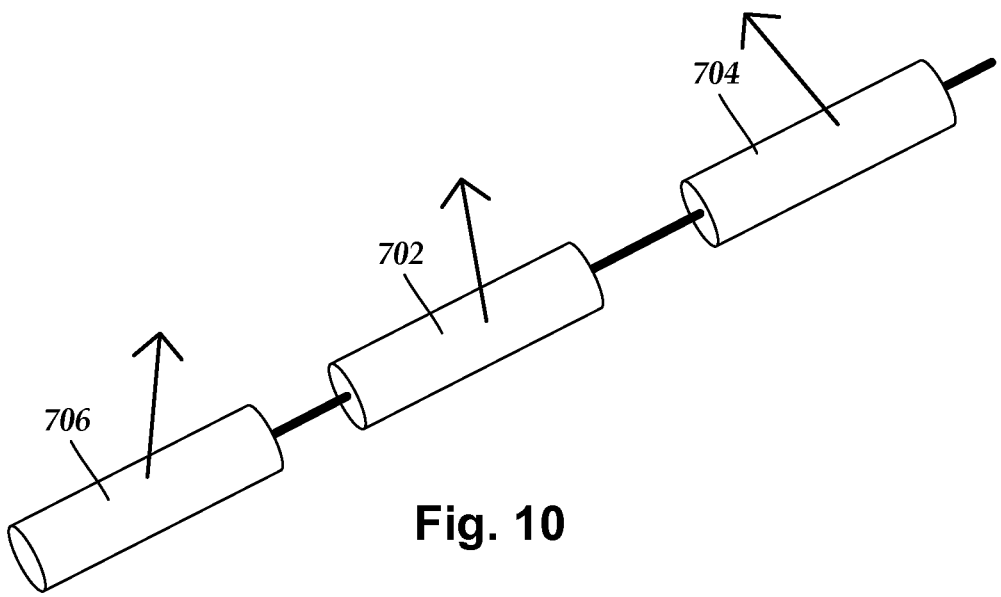
FIG. 10 is a schematic perspective view of one embodiment of the link magnets of FIG. 7 having staggered magnetization vectors, according to the invention.

Another way to compensate for twisting of flexible drive shaft 720 is to stagger the direction of the magnetization vector of the link magnets. FIG. 10 is a schematic perspective view of one embodiment of the link magnets 702, 704, and 706, each having magnetization vectors, indicated by arrows, that are staggered in orientation from one another to compensate for twisting of the flexible drive shaft 720.

As discussed above, it is desirable to be able to pump at least 5 liters of blood per minute in order to provide total hemodynamic support for a patient, although there are applications for blood pumps with less throughput. Without wishing to be held to any particular values, it is believed the pumping assembly 102 can pump 5 liters of blood per minute using one or more impellers having diameters of 12 mm and a magnet having a 2.5 mm diameter and a 15 mm length. The power to pump 5 liters per minute against a blood pressure head of nominally 100 mm Hg can be calculated using the formula:

$$P = p\, dV/dt;$$

where P=power in Watts; p=pressure head in $Nt/m^2$; and $dV/dt$=blood flow rate in $m^3/sec$. Using the known values 100 mm Hg=$1.3 \times 10^4$ $Nt/m^2$ and 5 liters/min=$8.3 \times 10^{-5}$ $m^3/sec$, then P=1.1 Watts of mechanical power. In other words, nominally 1.1 Watts of power are used to provide hemodynamic support to a human. The actual mechanical input power requirement may depend upon the efficiency of the impeller design. Some of the input power is often dissipated in backflow and eddy formation, or in more extreme phenomena, such as cavitation. Assuming a mechanical efficiency of 50%, 2.2 Watts of mechanical power can pump 5 liters of blood per minute.

Small electrical-motor-driven pumps are often less efficient than larger pumps because of Ohmic heat generated in the stator windings by the relatively high current needed to create the pumping torque. A larger winding volume often generates less heat for a given torque output. Thus, small electric pumps may use rapid blood flow to dissipate heat. In low blood flow, or near the wall of an artery, the pump temperature may rise, thereby resulting in shut down for safety.

One advantage of utilizing external stator windings is that heat build-up can occur external to the pumping assembly. Thus, heat build-up is less of a concern at the target pumping location. Additionally, as discussed above, external windings may not have the same size constraints as windings would have if the windings were disposed on a pumping assembly. Thus, the mass of the external windings may be orders of magnitude larger than windings disposed on an internal pumping assembly. Therefore, pumping assemblies utilizing external windings may be enabled to convert electrical energy to mechanical energy with less heat generated within the patient than pumping assemblies utilizing windings within the pumping assemblies.

When windings are disposed in a sheath surrounding link magnets as in FIG. 7, it may be an advantage to use a plurality of link magnets because increasing the number of link magnets may decrease the amount of current used to create a given torque. Also, increasing the number of link magnets may decrease the amount of heat generated by the motor. Furthermore, increasing the number of link magnets may increase the efficiency of the motor.

The mechanical power output of a two-pole magnet rotor driven by a rotating magnetic field generated by extracorporeal stator windings is given by:

$$P=\tau\omega;$$

where P=mechanical power output in Watts; τ=magnetic torque in Nt–m; ω=angular speed in rad/sec=2πf; and f=rotation speed in revolutions/sec, or Hz.

The mechanical torque for an oriented rare earth magnet for which magnetization is constant throughout the magnet volume (e.g., a neodymium-iron-boron magnet, or the like) is given by:

$$\tau=MVH;$$

where M=magnet magnetization in Tesla; V=magnet volume in m³; and H=winding magnetic field in Amp/m.

Without wishing to be held to any particular values, consider a magnet having a volume of $7.4\times10^{-8}$ m³ and magnetization of 1.5 Tesla rotating at 500 Hz with a power output of 2.2 Watts. Combining the previous two equations and solving for the winding magnetic field (H) in Amp/m, H=6,300 Amp/m, or about 80 Gauss.

The magnetic field from a three-phase winding is given by:

$$H=3NI/4\pi r;$$

where N=number of turns of each winding; I=current amplitude in Amps; r=distance from a winding to a center of the winding in m; and H=6,300 Amps/m. If r=6 inches=0.15 m, or about half the back-to-front width of a large person, and N=1000 turns, then solving for I yields I=4 Amps to create a magnetic field sufficient to power the magnet.

As shown in FIG. 5, in at least some embodiments the stator windings are disposed in bed railings. Again, without wishing to be held to any particular values, if the windings utilize a winding length of 20 inches wrapped into 1000 turns of AWG #10 copper magnet wire having a resistance of 0.001 Ohms/ft, then the winding bobbin may be about 3 inches by 3 inches and may double as bed railings. The total length of wire in each bobbin, accordingly, is about 5,000 feet and has a resistance of about 5 Ohms. At a maximum output of 5 liters per minute at 4 Amps (as calculated above), the heat generated in the windings=$I^2R/2$ (for sinusoids)=40 Watts, which is easily dissipated in bed railings in an ambient environment. Using heavier windings generates less heat. Design trade-offs may include, for example, the volume of the windings, the diameter of the bed railings, the temperature rise of the bed railings above ambient temperature (if any), and the power requirement of the external current supply. For example, in at least some embodiments, the windings may be actively cooled to enable a given magnetic field to be generated using smaller diameter windings.

As shown in FIG. 6, in at least some embodiments the stator windings are disposed in a garment. Smaller windings (e.g., windings disposed in a garment, as opposed to winding disposed in bed railings) may use less current to generate the same output, so smaller and lighter windings may be used. When winding length is reduced, resistance is also reduced. For example, when all of the distances of a three-phase winding are cut in half from the bed railing example, the generated heat may be reduced by a factor of eight, to 5 Watts (using the values from the previous calculations). Design trade-offs between heat generation, power output, and winding weight can be varied across a broad spectrum of winding geometries. As shown in FIGS. 7-10, in at least some embodiments the magnet is segmented into link magnets to enable the length of the magnet to be increased, while maintaining adequate flexibility to bend in patient vasculature. Doubling the overall length of the magnets may yield the same pump output with half the current and one-quarter the heat generation.

In at least some embodiments, the stator windings are formed from one or more magnetic materials including, for example, iron, nickel-iron, iron-cobalt-chromium, or the like. Forming the windings from one or more magnetic materials may increase the efficiency of the windings by reducing the winding volume or winding current needed to generate a magnet field sufficient to rotate the magnet. In at least some alternate embodiments, the external magnetic field is generated by one or more permanent magnets rotating external to the patient. In at least some embodiments, the one or more permanent magnets rotating external to the patient are rotated by a power source, such as a windings surrounding the permanent magnet, a conventional motor, or the like. In at least some embodiments, external magnets are mechanically rotated or tilted by conventional electric motors.

Figure 11:
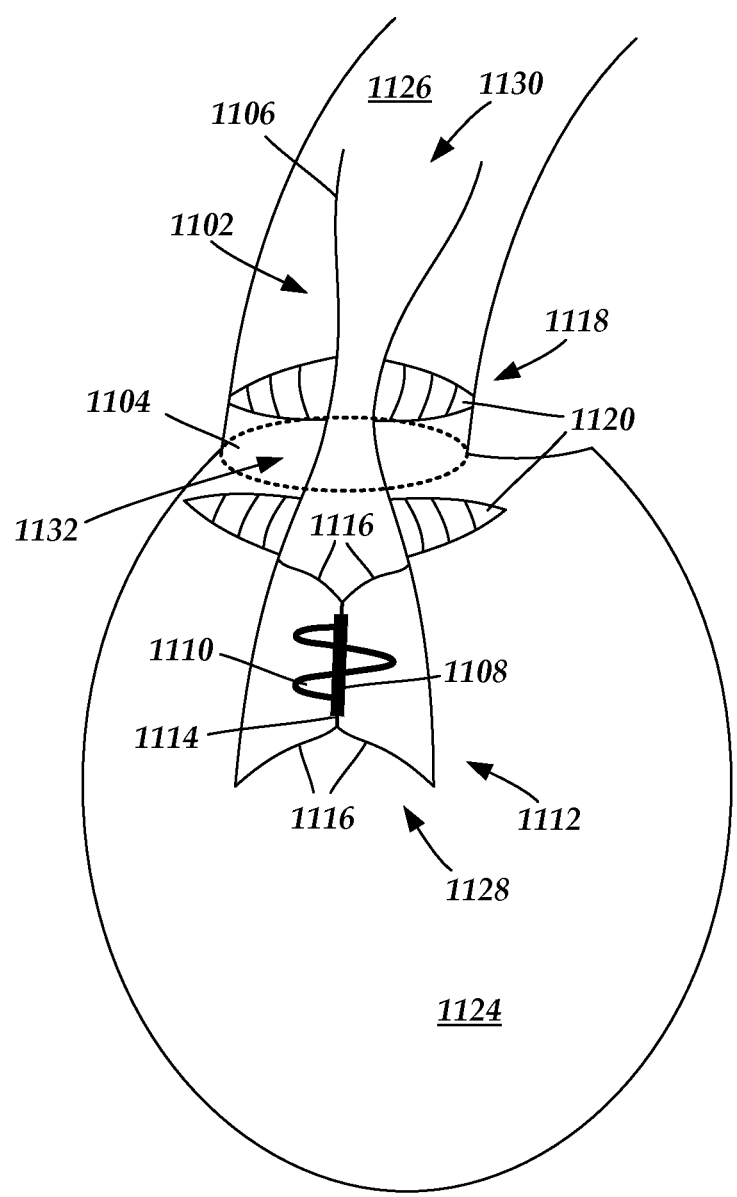
FIG. 11 is a schematic side view of a second embodiment of a pumping assembly disposed in patient vasculature, the pumping assembly disposed across an aortic valve, according to the invention.

FIG. 11 is a schematic side view of one embodiment of a pumping assembly 1102 disposed in the left ventricle of a patient's heart. Blood is pumped across the patient's aortic valve 1104 and into the patient's aorta. The pumping assembly 1102 includes an elongated pumping sleeve 1106. A rotatable magnet 1108 and one or more impellers 1110 are disposed in the pumping sleeve 1106. The one or more impellers 1110 are coupled to the one or more magnets 1108 such that rotation of the one or more magnets 1108 causes a corresponding rotation of the impellers 1110. In at least some embodiments, the one or more impellers 1110 are disposed, at least partially, over the one or more magnets 1108.

In at least some embodiments, the one or more magnets 1108 are coupled to a support structure 1112 that includes a shaft 1114 on which the one or more magnets 1108 rotate, and one or more struts 1116 that secure the one or more magnets 1108 to the pumping sleeve 1106 via the shaft 1114 and, optionally, bushings. In at least some embodiments, the one or more struts 1116 are configured and arranged to expand upon release from an insertion device. In at least some embodiments, the one or more struts 1116 expand such that the magnet 1108 is transversely centered within the pumping sleeve 1106. In at least some embodiments, at least one of the one or more impellers 1110 are coupled to the shaft 1114. In at least some embodiments, at least one of the one or more impellers 1110 are coupled to the shaft 1114 such that the at least one of the one or more impellers 1110 is separated axially from the one or more magnets 1108.

The pumping assembly 1102 also includes an anchoring arrangement 1118 for maintaining the positioning of the pumping sleeve 1106 at the target pumping location during operation. In at least some embodiments, the anchoring arrangement 1118 includes one or more stops (e.g., mesh stops) 1120 disposed along a length of the pumping sleeve 1106 such that, when the pumping sleeve 1106 is extended across the patient's aortic valve 1104, the one or more stops 1120 are positioned on one or more sides of the aortic valve 1104. In at least some embodiments, the one or more stops 1120 are configured and arranged to expand upon release from an insertion device. In at least some embodiments, the one or more stops 1120 expand such that the pumping assembly is transversely centered within the aortic valve 1104.

In at least some embodiments, the target pumping location is the region surrounding the patient's aortic valve 1104. In at least some embodiments, the target pumping location includes the patient's left ventricle 1124. In at least some embodiments, the target pumping location includes the patient's ascending aorta 1126. In at least some embodiments, the target pumping location extends from the patient's left ventricle 1124 to the patient's ascending aorta 1126. In at least some embodiments, the target pumping location extends from the patient's left ventricle 1124 to the patient's descending aorta (see e.g., FIG. 12).

The pumping sleeve 1106 has an inlet 1128 at a proximal end of the pumping sleeve 1106 and an outlet 1130 at a distal end of the pumping sleeve 1106. In at least some embodiments, the inlet 1128 is disposed in the patient's left ventricle 1124. In at least some embodiments, the outlet 1130 is disposed in the patient's ascending aorta 1126.

In at least some embodiments, the pumping sleeve 1106 is cylindrical. In at least some embodiments, the pumping sleeve 1106 is isodiametric. In at least some embodiments, the pumping sleeve 1106 has a reduced-diameter region 1132 disposed along the length of the pumping sleeve 1106 such that, when the pumping sleeve 1106 is extended across the patient's aortic valve 1104, the reduced-diameter region 1132 aligns with the patient's aortic valve 1104. In at least some embodiments, the reduced-diameter portion 1132 of the pumping sleeve 1106 facilitates reduction of damage to the aortic valve 1104 caused by the pumping assembly 1106 contacting the aortic valve 1104.

In at least some embodiments, at least one of the inlet 1128 or the outlet 1130 of the pumping sleeve 1106 are configured and arranged to expand upon release from an insertion device. In at least some embodiments, the pumping assembly 1102 operates without an electrical lead extending from the target pumping location to the entry point of the pumping assembly 1102 into the patient. In at least some embodiments, the pumping assembly 1102 operates without the shaft 1114 extending from the target pumping location to the entry point of the pumping assembly 1102 into the patient.

The pumping assembly 1102 is configured and arranged to pump blood downstream from the left ventricle 1128 through the pumping sleeve 1106. In at least some embodiments, the pumping assembly 1102 continuously pumps blood during operation. In at least some embodiments, the pumping assembly 1102 cycles between pumping blood and not pumping blood. In at least some embodiments, such as when the pumping assembly is disposed in the descending aorta, the pumping assembly 1102 cycles between pumping blood downstream (e.g., down the descending aorta) and pumping blood upstream (e.g., back up the aorta to one or more branching vessels, such as the left subclavian artery, the left common carotid artery, the brachiocephalic trunk, or the coronary arteries).

In at least some embodiments, there may be multiple target pumping locations. In at least some embodiments, a different pumping assembly may be disposed at each of the multiple target pumping locations. In at least some embodiments, a single pumping assembly may be used to pump blood at multiple target pumping locations. In at least some embodiments, a single set of stator windings may be used to generate a magnetic field for rotating a plurality of magnets (and impellers coupled to the magnets).

Figure 12:
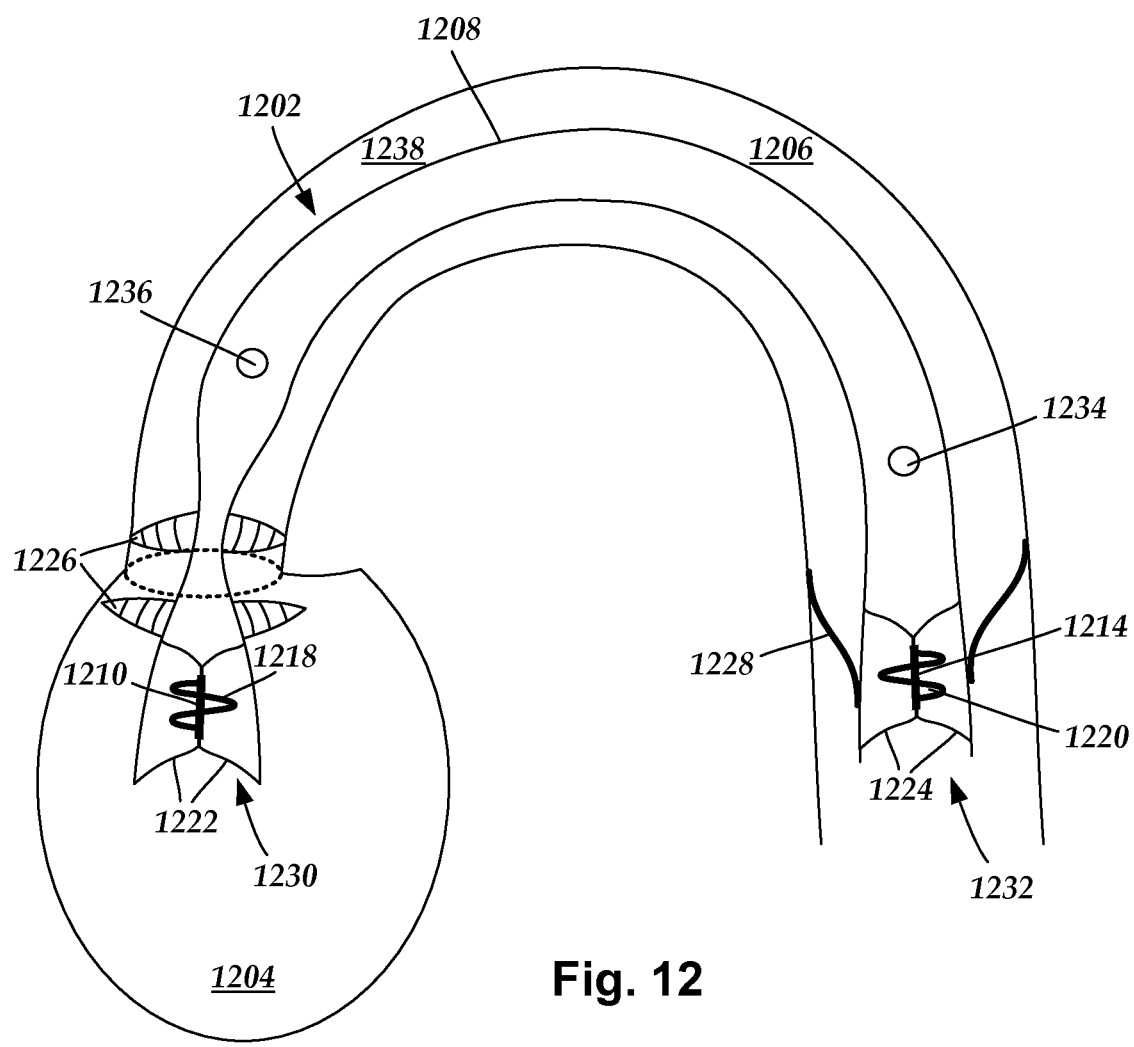
FIG. 12 is a schematic side view of a third embodiment of a pumping assembly disposed in patient vasculature, the pumping assembly including a plurality of magnets and impellers, according to the invention.

FIG. 12 is a schematic side view of one embodiment of a pumping assembly 1202 disposed in patient vasculature, such as a region extending from the patient's left ventricle 1204 to the patient's descending aorta 1206. The pumping assembly 1202 includes an elongated pumping sleeve 1208. A first magnet 1210 is positioned in the pumping sleeve 1208 such that the first magnet 1210 is disposed in the patient's left ventricle 1204 and a second magnet 1214 is positioned in the pumping sleeve 1208 such that the second magnet 1214 is positioned in the patient's descending aorta 1206. In at least some embodiments, one or more first impellers 1218 are coupled to the first magnet 1210 and one more second impellers 1220 are coupled to the second magnet 1214. In at least some embodiments, longitudinal axes of magnets 1210 and 1214 are aligned approximately in the same direction in space, so that a single external rotating magnetic field may simultaneously rotate both magnets 1210 and 1214 and both impellers 1218 and 1220.

In at least some embodiments, the magnets 1210 and 1214 are coupled to expandable magnet support structures 1222 and 1224, respectively, that secure the magnets 1210 and 1214 to the pumping sleeve 1208. The pumping assembly 1202 also includes anchoring arrangements 1226 and 1228 positioned in proximity to magnets 1210 and 1214, respectively, for maintaining the positioning of the pumping sleeve 1206 at the target pumping location(s) during operation.

The pumping sleeve 1208 has a first inlet 1230 at a proximal end of the pumping sleeve 1208 and a first outlet 1232 at a distal end of the pumping sleeve 1208. In at least some embodiments, the first inlet 1230 is positioned in the patient's left ventricle 1204 during operation of the pumping assembly 1202. In at least some embodiments, the first outlet 1232 is disposed in the patient's descending aorta 1206. In at least some embodiments, at least one of the first inlet 1230 or the first outlet 1232 of the pumping sleeve 1208 is configured and arranged to expand upon release from an insertion device.

In at least some embodiments, the pumping sleeve 1208 defines one or more additional inlets, such as second inlet 1234. The one or more additional inlets may be disposed anywhere along a length of the pumping sleeve 1208. In at least some embodiments, the second inlet 1234 is defined in the pumping sleeve 1208 such that the second inlet 1234 is disposed in the patient's descending aorta 1206 during operation. In at least some embodiments, the pumping sleeve 1208 defines one or more additional outlets, such as second outlet 1236. The one or more additional outlets may be disposed anywhere along a length of the pumping sleeve 1208. In at least some embodiments, the second outlet 1236 is defined in the pumping sleeve 1208 such that the second outlet 1236 is disposed in the patient's ascending aorta 1238 during operation.

In at least some embodiments, the one or more first impellers 1218 pump blood from the first inlet 1230 to the second outlet 1236 and to a region in proximity to the one or more second impellers 1220. In at least some embodiments, the one or more first impellers 1218 pump blood continuously during operation. In at least some embodiments, the one or more second impellers 1220 pump blood primarily between the second inlet 1234 to the first outlet 1232. In at least some embodiments, the one or more second impellers 1220 pump blood from the second inlet 1234 to the first outlet 1232 during systole. In at least some embodiments, the one or more second impellers 1220 pump blood from the first outlet 1232 to the second inlet 1234 to during diastole.

Figure 13:
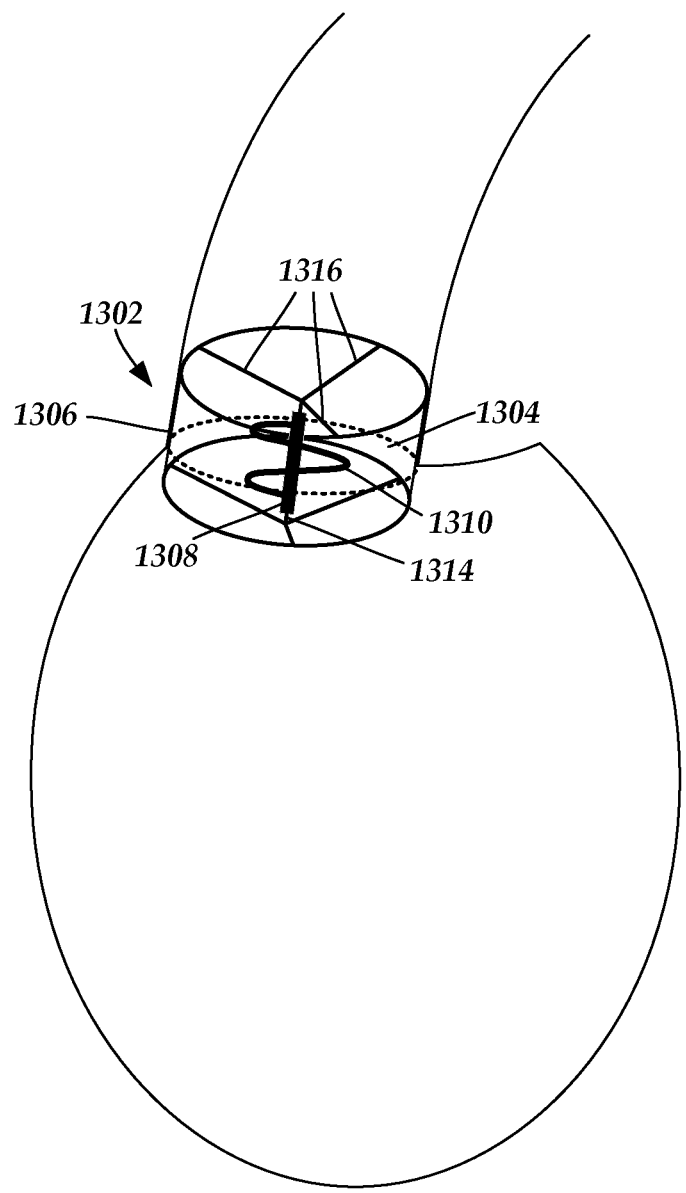
FIG. 13 is a schematic side view of a fourth embodiment of a pumping assembly disposed over the patient's aortic valve, according to the invention.

In at least some embodiments, the pumping assembly does not include a pumping sleeve. FIG. 13 is a schematic side view of one embodiment of a pumping assembly 1302 disposed over the patient's aortic valve 1304. The pumping assembly 1302 includes a support frame 1306, such as an expandable stent, to anchor the pumping assembly 1302 in position at a target pumping location, such as the patient's aortic valve 1304. A rotatable magnet 1308 and one or more impellers 1310 are disposed in the support frame 1306. In at least some embodiments, the one or more impellers 1310 are coupled to the magnet 1308. In at least some embodiments, the one or more impellers 1310 are coupled to the magnet 1308 such that rotation of the magnet 1308 causes a corresponding rotation of the impellers 1310. In at least some embodiments, the one or more impellers 1310 are disposed, at least partially, over the magnet 1308.

In at least some embodiments, the magnet 1308 is configured and arranged to rotate on a shaft 1314. In at least some embodiments, the pumping assembly 1302 includes one or more struts 1316 securing the magnet 1308 to the support frame 1306 via the shaft 1314. In at least some embodiments, the one or more struts 1316 are configured and arranged to expand upon release from an insertion device. In at least some embodiments, the one or more struts 1316 expand such that the magnet 1308 is transversely centered within the support frame 1306.

In at least some embodiments, the pumping assembly 1302 is configured and arranged to pump blood continuously across the aortic valve 1304. In at least some embodiments, the external stator windings may be implanted in the patient in proximity to the aortic valve 1304 including, for example, the pericardial space, right atrium, a subcutaneous pocket formed in the thorax. In at least some embodiments, an associated electronic subassembly and controllers may also be implanted in the patient in proximity to the aortic valve 1304. In at least some embodiments, the pumping assembly 1302 and stator windings may be powered by implanted batteries that inductively recharged while implanted in the patient.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A percutaneous pumping system for providing hemodynamic support to a patient, the percutaneous pumping system comprising:
    a pumping sleeve having a length, a distal end, and a proximal end, the pumping sleeve defining a lumen extending along the length of the pumping sleeve from the proximal end to the distal end, the pumping sleeve configured and arranged for insertion into patient vasculature;
    at least one rotatable magnet disposed in the pumping sleeve, wherein the at least one first magnet is configured and arranged to be driven to rotate by a magnetic field generated external to the pumping sleeve;
    at least one impeller coupled to the at least one magnet, wherein rotation of the at least one magnet causes a corresponding rotation of the at least one impeller;
    a stator spaced apart from the pumping sleeve; and
    an anchoring arrangement coupled to the pumping sleeve, the anchoring arrangement configured and arranged to anchor the pumping sleeve at a target pumping location when the pumping sleeve is inserted into patient vasculature.

2. The percutaneous pumping system of claim 1, wherein the stator comprises at least two magnetic field windings configured and arranged to provide the magnetic field.

3. A percutaneous pumping system, for providing hemodynamic support to a patient, the percutaneous pumping system comprising:
    a pumping sleeve having a length, a distal end, and a proximal end, the pumping sleeve defining a lumen extending along the length of the pumping sleeve from the proximal end to the distal end, the pumping sleeve configured and arranged for insertion into patient vasculature;
    at least one rotatable magnet disposed in the pumping sleeve, wherein the at least one first magnet is configured and arranged to be driven to rotate by a magnetic field generated external to the pumping sleeve;
    at least one impeller coupled to the at least one magnet, wherein rotation of the at least one magnet causes a corresponding rotation of the at least one impeller;
    an anchoring arrangement coupled to the pumping sleeve, the anchoring arrangement configured and arranged to anchor the pumping sleeve at a target pumping location when the pumping sleeve is inserted into patient vasculature; and
    at least two magnetic field windings disposed external to the patient during operation of the percutaneous pumping system, the windings configured and arranged to provide the magnetic field.

4. The percutaneous pumping system of claim 2, wherein the at least two magnetic field windings are disposed in bed railings.

5. The percutaneous pumping system of claim 2, wherein the at least two magnetic field windings are disposed in a garment that is wearable by the patient.

6. The percutaneous pumping system of claim 1, wherein the pumping sleeve comprises a reduced-diameter portion configured and arranged for positioning in proximity to the patient's aortic valve during operation of the percutaneous pumping system.

7. The percutaneous pumping system of claim 1, further comprising a shaft along which the at least one magnet rotates, wherein the shaft does not extend beyond the pumping sleeve.

8. The percutaneous pumping system of claim 1, further comprising at least one strut configured and arranged for anchoring the at least one magnet to the pumping sleeve.

9. The percutaneous pumping system of claim 1, wherein the anchoring arrangement comprises at least one of at least one strut or at least one mesh stop configured and arranged for maintaining the pumping sleeve at a target pumping location.

10. The percutaneous pumping system of claim 1, wherein the at least one magnet comprises a plurality of link magnets coupled to one another in series.

11. The percutaneous pumping system of claim 1, wherein the percutaneous pumping system is configured and arranged for insertion into patient vasculature via an insertion device with a bore that is no greater than 9 French.

12. The percutaneous pumping system of claim 1, wherein the at least one impeller is expandable.

13. The percutaneous pumping system of claim 1, wherein the at least one impeller is coupled directly to the at least one magnet.

14. The percutaneous pumping system of claim 1, wherein the at least one impeller is coupled to the at least one magnet such that the at least one impeller is disposed over at least a portion of the at least one magnet.

15. The percutaneous pumping system of claim 1, further comprising a safety line coupled to the pumping sleeve, the safety line configured and arranged to extend along patient vasculature to a region external to the patient.

16. The percutaneous pumping system of claim 1, wherein the at least one magnet comprises a first magnet and a second magnet, wherein the first magnet and the second magnet are each disposed in the pumping sleeve, and wherein the first magnet and the second magnet are both configured and arranged to be driven to rotate by the magnetic field generated external to the pumping sleeve.

17. The percutaneous pumping system of claim 16, wherein the at least one impeller comprises a first impeller and a second impeller, wherein the first impeller is coupled to the first magnet such that rotation of the first magnet causes a corresponding rotation of the first impeller, and wherein the second impeller is coupled to the second magnet such that rotation of the second magnet causes a corresponding rotation of the second impeller.

18. The percutaneous pumping system of claim 2, wherein the at least two magnetic field windings are implanted in the patient.

\* \* \* \* \*

UNITED STATES PATENT AND TRADEMARK OFFICE
CERTIFICATE OF CORRECTION

| | | |
|---|---|---|
| PATENT NO. | : 8,734,508 B2 | Page 1 of 1 |
| APPLICATION NO. | : 12/967856 | |
| DATED | : May 27, 2014 | |
| INVENTOR(S) | : Roger N. Hastings et al. | |

It is certified that error appears in the above-identified patent and that said Letters Patent is hereby corrected as shown below:

IN THE CLAIMS:

Column 18
Line 17, after "Claim 18", insert the originally filed Claim 18 --18. The percutaneous pumping system of claim 1 wherein the pumping sleeve comprises at least one aperture defined along the length of the pumping sleeve between the proximal end of the pumping sleeve and the distal end of the pumping sleeve, the at least one aperture configured and arranged to permit patient blood to pass into, and through, the pumping sleeve--.

Signed and Sealed this
Sixteenth Day of December, 2014

Michelle K. Lee
*Deputy Director of the United States Patent and Trademark Office*